(12) United States Patent
Mishima et al.

(10) Patent No.: US 6,527,756 B1
(45) Date of Patent: Mar. 4, 2003

(54) DISPOSABLE DIAPER

(75) Inventors: Yoshitaka Mishima, Kagawa-ken (JP); Hiroyuki Tanji, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 180 days.

(21) Appl. No.: 09/662,576

(22) Filed: Sep. 15, 2000

(30) Foreign Application Priority Data

Sep. 16, 1999 (JP) .......................................... 11-262170

(51) Int. Cl.[7] ................................................ A61F 13/15
(52) U.S. Cl. ............................ 604/385.19; 604/385.24; 604/385.27
(58) Field of Search .................. 604/385.01, 385.16, 604/385.19, 385.22, 385.24, 385.27, 385.28

(56) References Cited

U.S. PATENT DOCUMENTS

| | | | |
|---|---|---|---|
| 5,462,541 A | * 10/1995 | Bruemmer et al. | 604/391 |
| 5,601,543 A | * 2/1997 | Dreier et al. | 604/385.1 |
| 5,667,503 A | * 9/1997 | Roe et al. | 604/385.1 |
| 5,817,086 A | * 10/1998 | Kling | 604/385.2 |
| 5,904,674 A | 5/1999 | Bonjour | |
| 6,150,485 A | * 9/2000 | Gustafsson et al. | 604/385.19 |
| 6,133,501 A | * 10/2000 | Hallock et al. | 604/369 |
| 6,168,583 B1 | * 1/2001 | Tanji et al. | 604/385.14 |
| 6,168,584 B1 | * 1/2001 | Allen et al. | 604/385.19 |
| 6,328,724 B1 | * 12/2001 | Ronnberg et al. | 604/385.24 |
| 6,329,565 B1 | * 12/2001 | Dutkiewicz et al. | 604/378 |
| 2001/0004689 A1 | * 6/2001 | Otsubo | 604/385.19 |

FOREIGN PATENT DOCUMENTS

| | | |
|---|---|---|
| EP | 0 615 737 A2 | 9/1994 |
| EP | 0 908 162 A2 | 4/1999 |
| GB | 2 297 565 A | 8/1996 |
| JP | 5-277149 | 10/1993 |
| WO | WO 97/17920 | 5/1997 |
| WO | WO 98/53779 | 12/1998 |
| WO | WO 99/65436 | 12/1999 |

\* cited by examiner

*Primary Examiner*—John G. Weiss
*Assistant Examiner*—Michael Bogart
(74) *Attorney, Agent, or Firm*—Baker & Daniels (57) ABSTRACT

A diaper having an absorbent body including a topsheet, a backsheet, a core disposed therebetween and a first liquid-barrier wall lying in a rear half section of the body and extending above an upper surface of the topsheet so as to define a first opening in a substantially central zone of the first liquid-barrier wall, and the body further includes a second liquid-barrier wall lying in a front half section of the body in one-behind-another relationship with the first liquid-barrier wall so as to define a second opening in a substantially central zone of the second liquid-barrier wall so that urine discharged into the second opening may be absorbed by the core through the topsheet and feces discharged into the first opening may be absorbed by the core through the topsheet.

7 Claims, 8 Drawing Sheets

DISPOSABLE DIAPER

BACKGROUND OF THE INVENTION

This invention relates to a disposable diaper for absorption and containment of excretion.

Japanese Patent Application Disclosure No. 1993-277149 describes a disposable diaper comprising a liquid-pervious topsheet, a liquid-impervious backsheet, a liquid-absorbent core disposed between these two sheets and an annular liquid-resistant upper sheet extending above the outer surface of the topsheet. The upper sheet is joined along its outer peripheral edge to the outer surface of the topsheet and formed substantially in its central zone with a longitudinally extending opening which is, in turn, provided along its peripheral edge with a longitudinally stretchable elastic member. With this prior art diaper, it is possible to prevent undesirable leakage of excretion disposed thereon from occurring along transversely opposite side edges and/or along longitudinally opposite ends of the diaper by the annular upper sheet extending above the outer surface of the topsheet and bonded along its peripheral edge to the topsheet.

However, the Japanese Patent Application Disclosure No. 1993-277149 has a problem in that, after urine and feces have been discharged into the opening, an amount of urine flowing on the topsheet may be mixed with loose passage, watery feces or even relatively solid feces since it is impossible for such known diaper to separate feces from urine. Consequently even relatively solid feces may become watery and give the wearer an uncomfortable feeling if this watery mixture comes in contact with a wearer's skin.

SUMMARY OF THE INVENTION

It is an object of this invention to provide a disposable diaper that prevents undesirable leakage of urine as well as feces discharged on a diaper from occurring along both transversely opposite side edges and longitudinally opposite ends of the diaper, on one hand, and prevents urine and feces from being mixed together so that a wearer may be free from any uncomfortable feeling, on the other hand.

According to this invention, there is provided a disposable diaper having an absorbent body comprising: a liquid-pervious topsheet; a liquid-impervious backsheet; a liquid-absorbent core disposed therebetween; an annular first liquid-barrier wall extending above an outer surface of the topsheet, the first liquid-barrier wall being joined along a lower peripheral edge thereof to the body so as to define a first opening substantially in a central zone of the first liquid-barrier wall and an upper peripheral edge of the first liquid-barrier wall is elastically stretchable along the first opening; the first liquid-barrier wall lying in a rear half section of the body extending from vicinity of a center line bisecting a longitudinal dimension of the body toward the rear end portion of the body; an annular second liquid-barrier wall lying in a front half section of the body extending from the centerline toward a front end portion of the body in one-behind-another relationship with the first liquid-barrier wall; and the second liquid-barrier wall having an outer peripheral edge portion joined to the body so as to define a second opening in a substantially central zone of the second liquid-barrier wall and an inner peripheral edge portion having an elastic stretchability along the second opening.

According to one preferred embodiment of this invention, the disposable diaper further comprises an annular third liquid-barrier wall spanning the front and rear half sections and extending around the first and second liquid-barrier walls wherein the third liquid-barrier wall has its outer peripheral edge portion fixed to the panel in the vicinity of its periphery so as to define a third opening in a substantially central zone of the third liquid-barrier wall and its inner peripheral edge portion being elastically stretchable along the third opening.

With the disposable diaper according to this invention, the first liquid-barrier wall prevents urine and feces discharged from being mixed together even when any one of such urine and feces tends to flow. Additionally, the first and second liquid-barrier walls extend on the outer surface of the topsheet and thereby prevent leak of urine and feces discharged onto the diaper from occurring along the transversely opposite side edges as well as along the longitudinally opposite ends of the diaper.

In the case of the diaper having the third liquid-barrier wall extending around the first and second liquid-barrier walls, this third liquid-barrier wall reliably functions as barrier against any urine and feces that possibly leaks beyond the first and second liquid-barrier walls and thereby further improves the preventive effect of the diaper against leakage of urine as well as feces.

DETAILED DESCRIPTION OF THE PREFERRED EMBODIMENT

Details of a disposable diaper according to this invention will be more fully understood from the description given hereunder with reference to the accompanying drawings.

Figure 1:
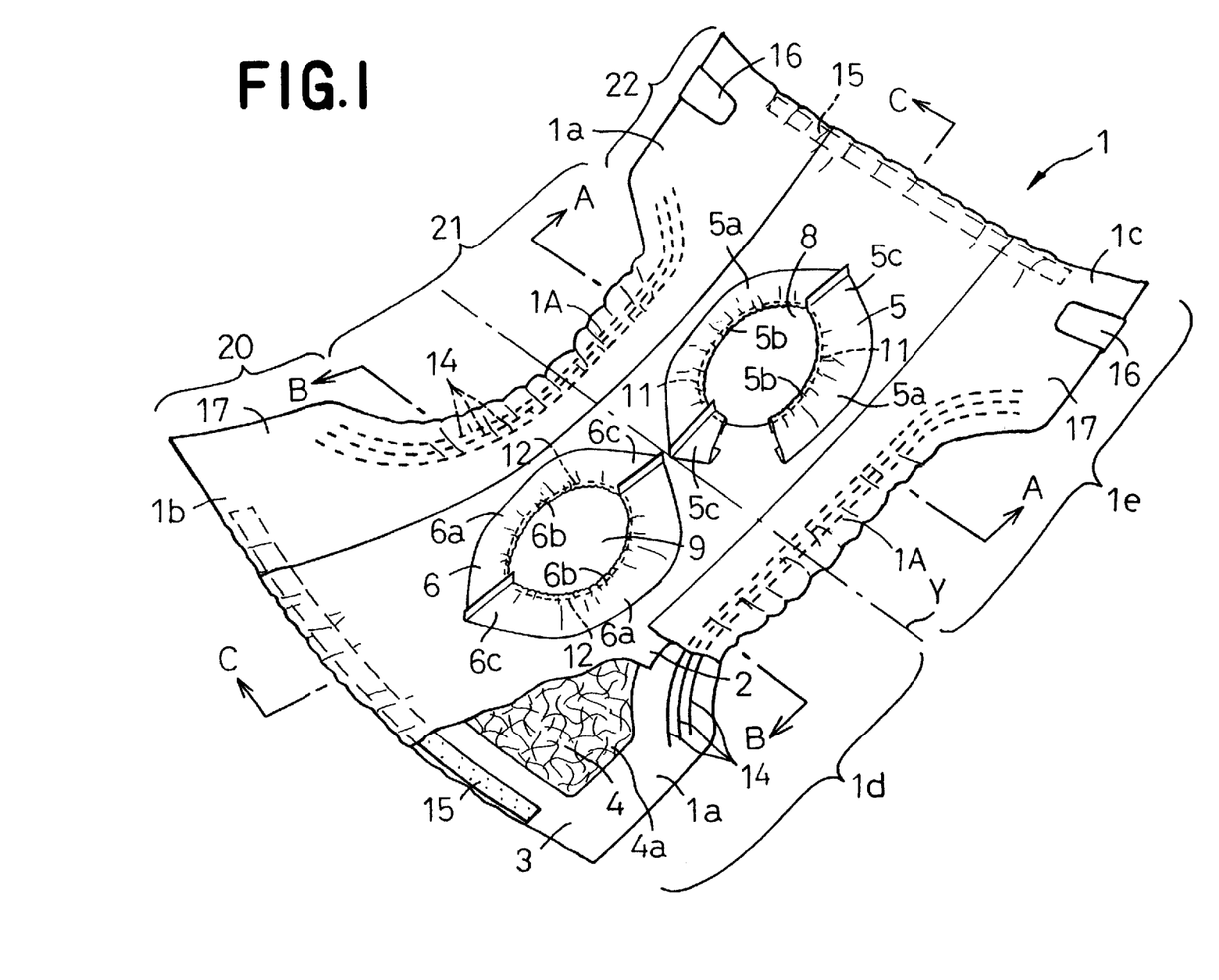
FIG. 1 is a perspective view showing a partially cutaway disposable diaper according to this invention.

FIG. 1 is a perspective view showing a partially cutaway disposable diaper according to this invention. A diaper is provided with an absorbent body in the form of a laminated panel. The body 1 comprises a liquid-pervious topsheet 2, a liquid-impervious backsheet 3, a liquid-absorbent core 4 disposed between these top- and backsheets 2, 3, an annular first liquid-barrier wall 5 extending above the upper surface of the topsheet 2 and an annular second liquid-barrier wall 6 extending above the upper surface of the topsheet 2 in one-behind-another relation with the first liquid-barrier wall 5. The body 1 is longitudinally composed of a front waist region 20, a rear waist region 22 and a crotch region 21 extending between these front and rear waist regions 20, 22. The body 1 has transversely opposite side edge portions 1a, 1a longitudinally extending parallel to each other and curved, in the crotch region 21, inwardly of the body 1 so as to describe circular arcs and longitudinally opposite end portions 1b, 1c transversely extending parallel to each other. The body 1 is further provided along its side edge portions 1a, 1a with a pair of longitudinally extending liquid-resistant side sheets 17, 17 opposed to and spaced from each other.

The first liquid-barrier wall 5 lies in a rear half section 1e of the body 1 which section extends from the vicinity of a center line Y bisecting a longitudinal dimension of the body 1 toward the rear end portion 1c of the body 1. The first liquid-barrier wall 5 comprises a pair of symmetrical halves each having a lower peripheral edge portion 5a describing a circular arc, an upper peripheral edge portion 5b describing also a circular arc inside the lower peripheral edge portion 5a and longitudinally opposite ends 5c, 5c joined to each other.

In a substantially central zone of the first liquid-barrier wall 5, a longitudinal first opening 8 is defined, in which approximately one half of the crotch region 21 and approximately one half of the rear waist region 22 are exposed. Obviously, the topsheet 2 is exposed in this first opening 8. An elastically stretchable member 11 is secured under tension to the first liquid-barrier wall 5 along its upper peripheral edge portion 5b.

The second liquid-barrier wall 6 lies in a front half section id of the body 1 which section extends from the vicinity of the center line Y bisecting a longitudinal dimension of the body 1 toward the front end portion 1b of the body 1. The second liquid-barrier wall 6 comprises a pair of symmetrical halves each having an lower peripheral edge portion 6a describing a circular arc, an upper peripheral edge portion 6b describing also a circular arc inside the lower peripheral edge portion 6a and longitudinally opposite end portions 6c, 6c joined to each other.

In a substantially central zone of the second liquid-barrier wall 6, a longitudinal second opening 9 is defined, in which approximately one half of the crotch region 21 and approximately one half of the front waist region 20 are exposed. It will be obviously understood that, in this second opening 9, the topsheet 2 is exposed. An elastic member 12 is secured under tension to the second liquid-barrier wall 6 along its upper peripheral edge portion 6b.

The body 1 is provided along its side edge portions 1a, 1a with longitudinally extending elastic members 14, 14 secured under tension thereto and along its front and rear end portions 1b, 1c with transversely extending ribbon-like elastic members 15, 15, respectively, disposed between the top- and backsheets 2,3 and secured under tension to the inner surface of at least one of these two sheets 2, 3. The elastic members 14, 14 are intended to be associated with leg-openings and the elastic member 15, 15 are intended to be associated with a waist-opening. In the rear waist region 22, a pair of tape fasteners 16, 16 extending inwardly of the body 1 are attached to the side edge portions 1a, 1a of the body 1, respectively.

Referring to FIG. 1, gathers are formed along the upper peripheral edge portions 5b, 6b of the first and second liquid-barrier walls 5, 6, the transversely opposite side edge portions 1a, 1a as well as longitudinally opposite end portions 1b, 1c of the body 1 as the elastic members 11, 12 respectively for the first and second liquid-barrier walls 5, 6, the elastic members 14, 14 for the leg-opening and the elastic members 15, 15 for the waist-opening are relieved of the tension.

Figure 2:
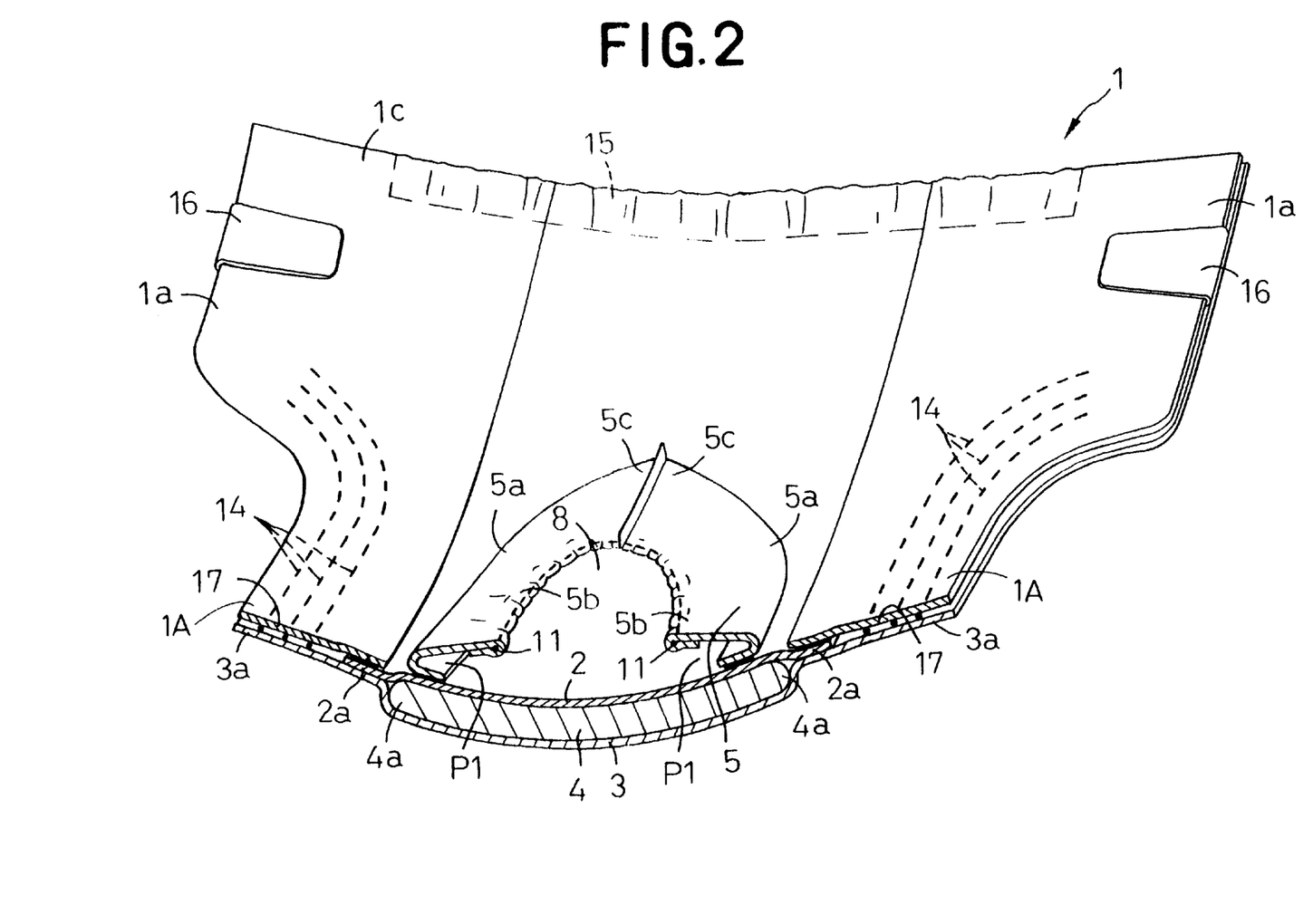
FIG. 2 is a perspective view showing the diaper partially in a sectional view taken along line A—A in FIG. 1.
Figure 3:
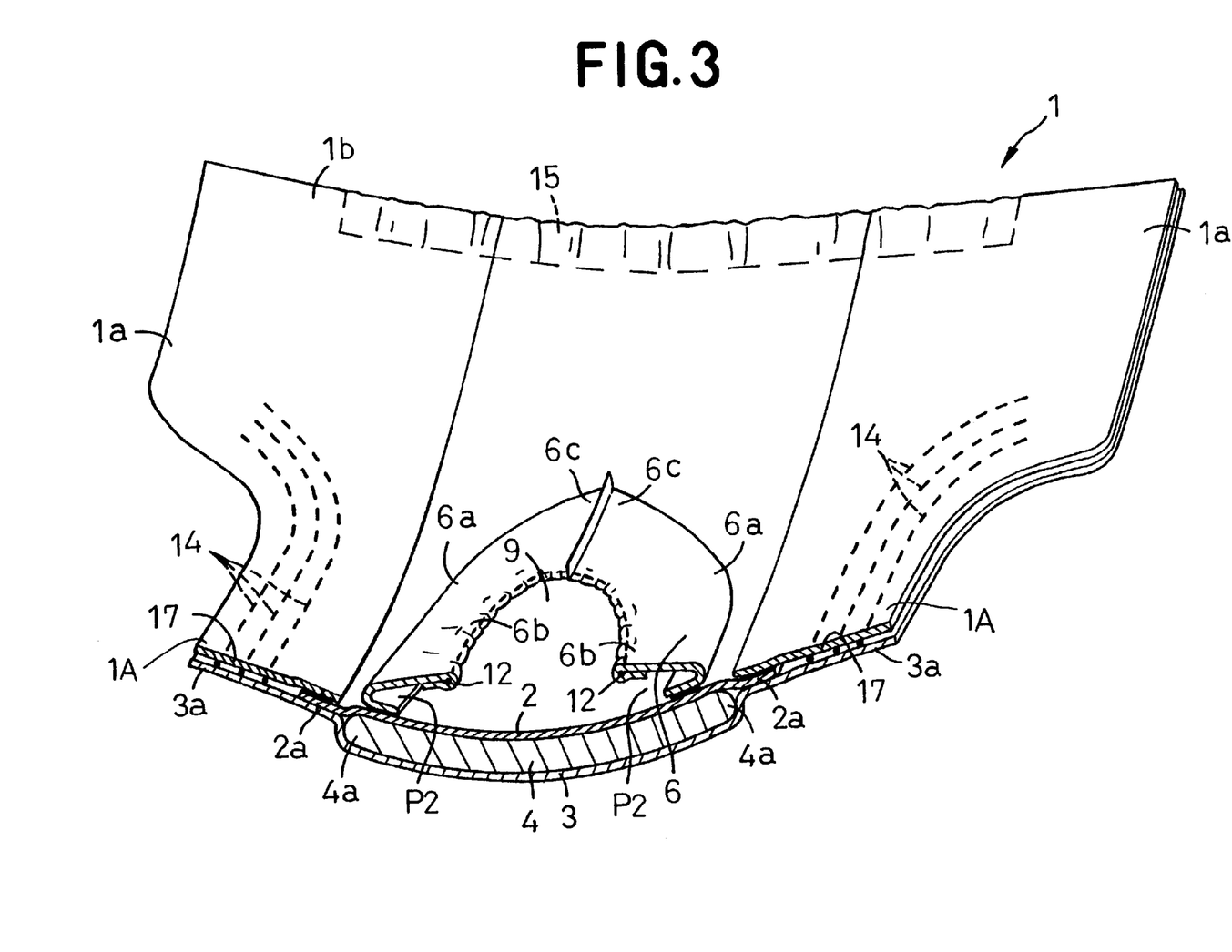
FIG. 3 is a perspective view showing the diaper partially in a sectional view taken along line B—B in FIG. 1.
Figure 4:
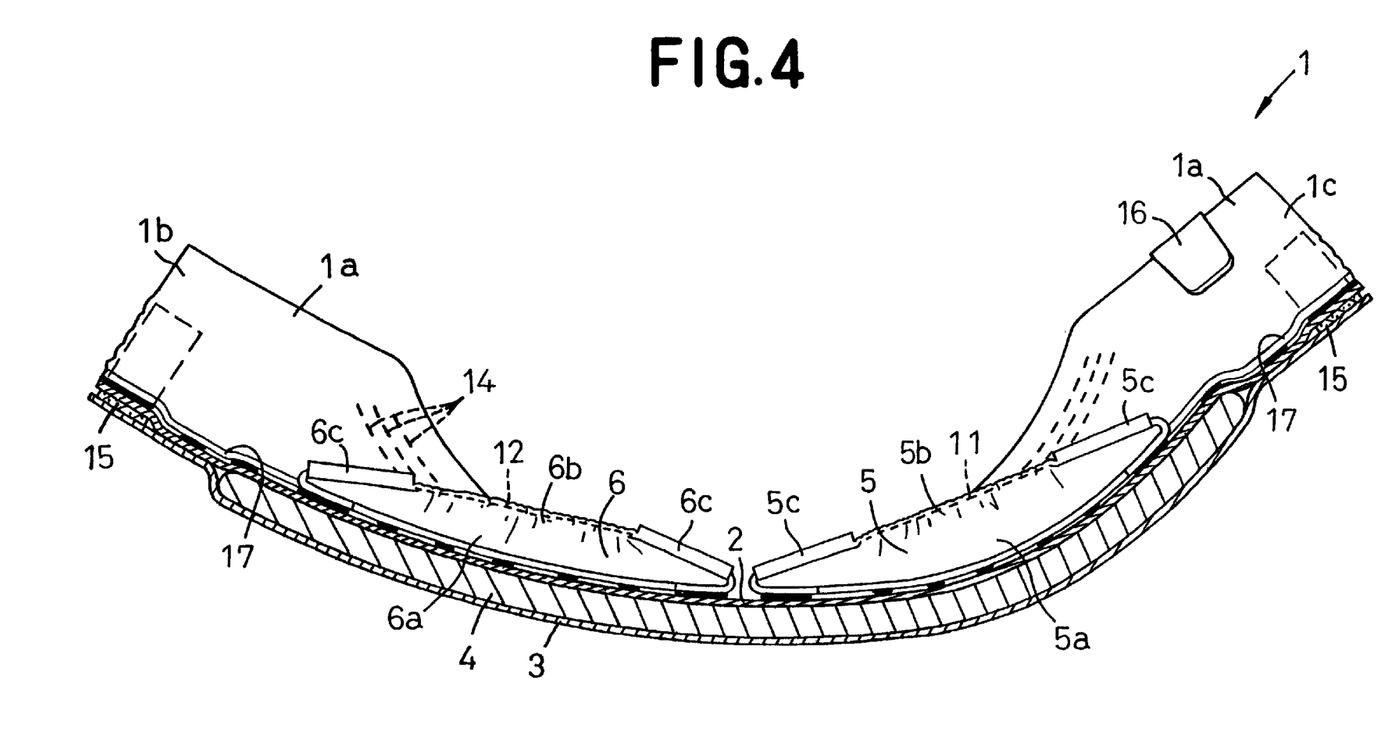
FIG. 4 is a sectional view taken along line C—C in FIG. 1.

FIGS. 2 and 3 are perspective views showing the diaper partially in sectional views taken along line A—A and a line B—B in FIG. 1, respectively, and FIG. 4 is a sectional view taken along line C—C in FIG. 1. The lower peripheral edge portion 5a of the first liquid-barrier wall 5 is partially folded inwardly of the body 1 and fixed to the lower surface of the topsheet 2 and the upper peripheral edge portion 5b of the first liquid-barrier wall 5 is also partially folded inwardly of the body 1 to cover the elastic member 11. The longitudinally opposite ends 5c, 5c of the first liquid-barrier wall 5 are against and bonded to each other along a line extending outward longitudinally of the body 1.

Similarly, the lower peripheral edge portion 6a of the second liquid-barrier wall 6 is partially folded inwardly of the body 1 and fixed to the outer surface of the topsheet 2 and the upper peripheral edge portion 6b of this second liquid-barrier wall 6 is partially folded inwardly of the body 1 so as to cover the elastic member 12. The longitudinally opposite ends 6c, 6c are put against and joined to each other along a line extending outward longitudinally of the body 1.

The first liquid-barrier wall 5 cooperates with the topsheet 2 to form a pocket P1 adapted to be opened inwardly of the body 1 and the second liquid-barrier wall 6 cooperates with the topsheet 2 to form a pocket P2 also adapted to be opened inwardly of the body 1 as the body 1 is curved longitudinally and transversely thereof with its inner surface inside.

The side edge portions 2a, 2a of the topsheet 2 transversely extends outward slightly beyond the side edges 4a, 4a of the core 4. The side edge portions 3a, 3a of the backsheet 3 and the side sheets 17, 17 extend outward transversely as well as longitudinally beyond the side edge portions 2a, 2a of the topsheet 2. The side edge portions 2a, 2a of the topsheet 2 are disposed between the backsheet 3 and the side sheets 17, 17 and joined to the inner surface of at least one of the backsheet 3 and the side sheets 17, 17. The backsheet 3 and the side sheets 17, 17 are joined together in zones along which these backsheet 3 and side sheets 17, 17 overlap one another, so as to form a pair of gasket cuffs 1A. The elastic members 14, 14 for the respective leg-openings are disposed between the backsheet 3 and the side sheet 17, 17 and secured under tension to the inner surface of at least one of these two sheets 3, 17. The core 4 is fixed to the inner surface of at least one of the top- and backsheets 2, 3.

The body 1 forms the pair of leg-openings and the waist-opening (not shown) as the tape fasteners 16, 16 are anchored to the strip of target tape attached to the upper surface of the backsheet 3 in the front waist region 20 by means of pressure-sensitive adhesive applied on the inner surfaces of free end portions of the respective tape fasteners 16, 16.

Urine discharged into the second opening 9 lying in the front half section 1d of the body 1 is absorbed by the core 4 through the topsheet 2 and feces discharged into the first opening 8 lying in the rear half section 1e of the body 1 is also absorbed by the core 4 through the topsheet 2. The first and second liquid-barrier wall 5, 6 function to separate a urine absorbing zone and a feces absorbing zone respectively defined in the front and rear half sections 1d, 1e of the body 1 from each other. In other words,the first and second liquid-barrier wall 5, 6 prevents feces discharged into the first opening 8 from moving into the second opening 9 or to prevent urine discharged into the second opening 9 from flowing into the first opening 8 and thereby to prevent urine and feces from being mixed together. Feces discharged onto the body 1 can be received by the pocket P1 and, therefore, even if discharged feces is of a large amount, movement of feces into the second opening 8 can be reliably avoided.

The side edges 3a, 3a of the backsheet 3 and the side sheets 17 extend transversely outward beyond the side edges 2a, 2a of the topsheet 2 and this arrangement is effective to prevent urine and feces from permeating the side edges 3a, 3a of the backsheet 3 as well as the gasket cuffs 17, 17 even if urine and feces permeate the side edges 2a, 2a of the topsheet 2.

Figure 5:
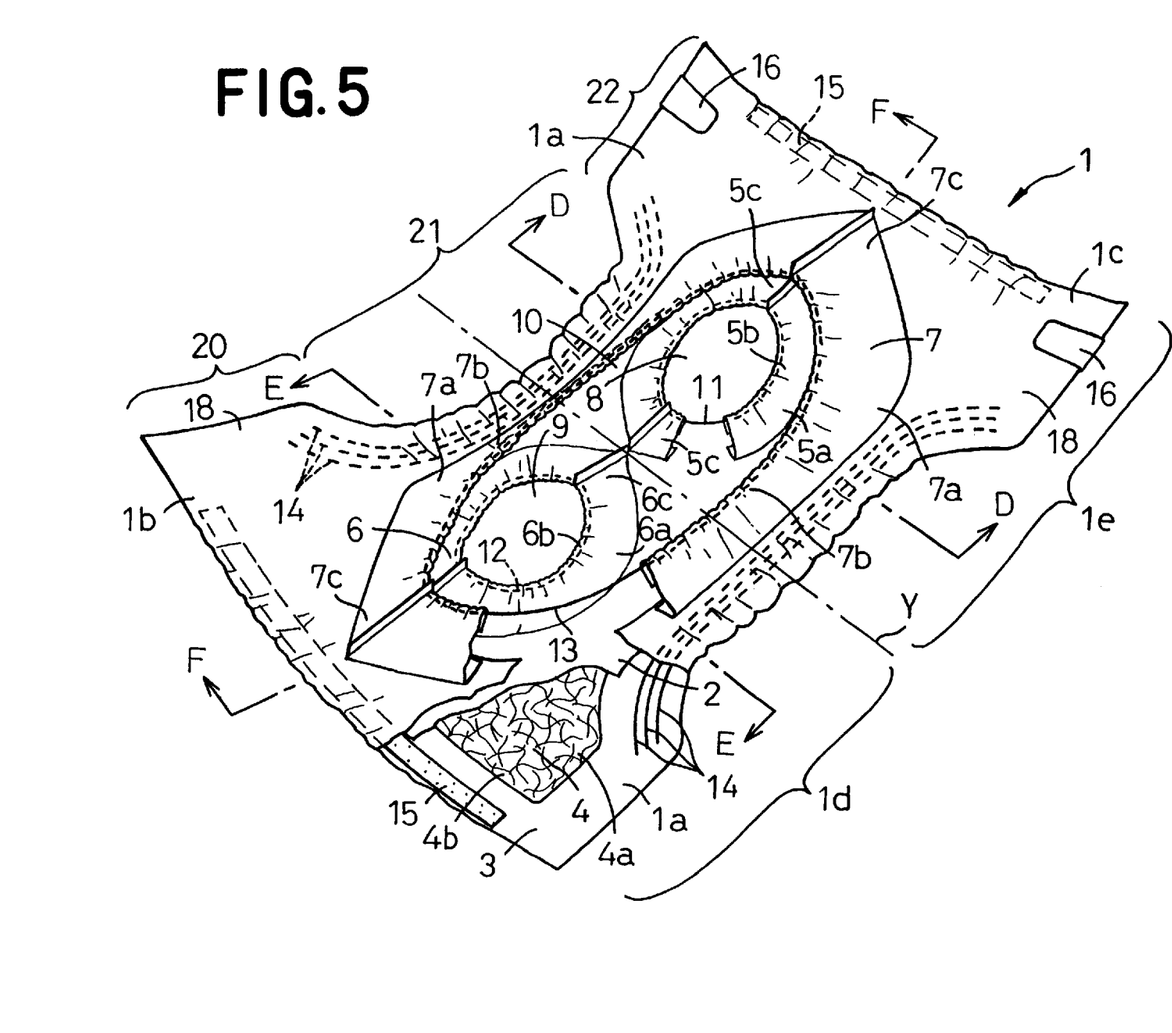
FIG. 5 is a view similar to FIG. 1 but showing another embodiment of the diaper.

FIG. 5 is a view similar to FIG. 1 but showing another embodiment of the disposable diaper according to this invention. This diaper is similar to the diaper of FIG. 1, where components similar to those previously described have the same reference numeral and its description is omitted. The body 1 according to this embodiment further comprises an annular third liquid-barrier wall 7 extending above the upper surface of the a topsheet 2 around the first and second liquid-barrier wall 5, 6.

The third liquid-barrier wall 7 spans the front and rear half sections 1d, 1e of the body 1 and comprises a pair of symmetrical halves each has a lower peripheral edge portion 7a describing a circular arc, an upper peripheral edge portion 7b describing also a circular arc inside the lower peripheral edge portion 7a and longitudinally opposite ends 7c, 7c joined to each other.

In a substantially central zone of the third liquid-barrier wall 7, a longitudinal third opening 10 is defined, in which approximately one half of the front waist region 20 and approximately one half of the rear waist region 22 are exposed. The upper peripheral edge 7b of the third liquid-barrier wall 7. lies outside both the upper peripheral edges 5b, 6b of the first and second liquid-barrier wall 5, 6, i.e., the third opening 10 surrounds the first and second openings 8, 9. In the third opening 10, the entire area of the second opening 9 is exposed in the front half section 1d of the body 1 and the entire area of the first opening 8 is exposed in the rear half section 1e of the body 1. An elastic member 13 is secured under tension to the third liquid-barrier wall 7 along its upper peripheral edge portion 7b. A pair of liquid-resistant second topsheet 18 extend laterally outward from the lower peripheral edges 7a, 7a of the third liquid-barrier wall 7, 7.

Referring to FIG. 5, gathers are formed along the upper peripheral edge portion 7b of the third liquid-barrier wall 7, as the elastic member 13 for the third liquid-barrier wall 7 is relieved of the tension.

Figure 6:
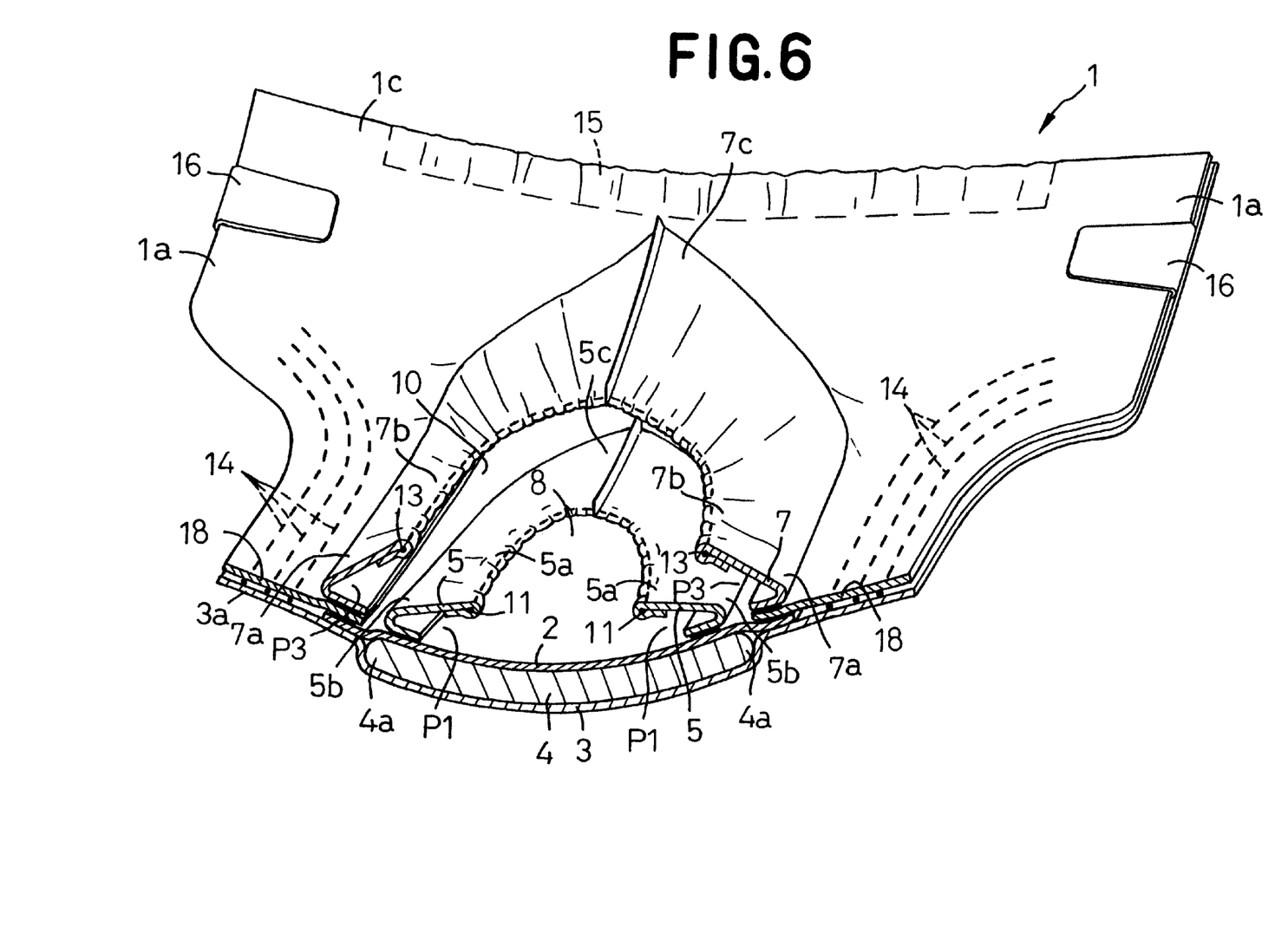
FIG. 6 is a perspective view showing the diaper partially in a sectional view taken along line D—D in FIG. 5.
Figure 7:
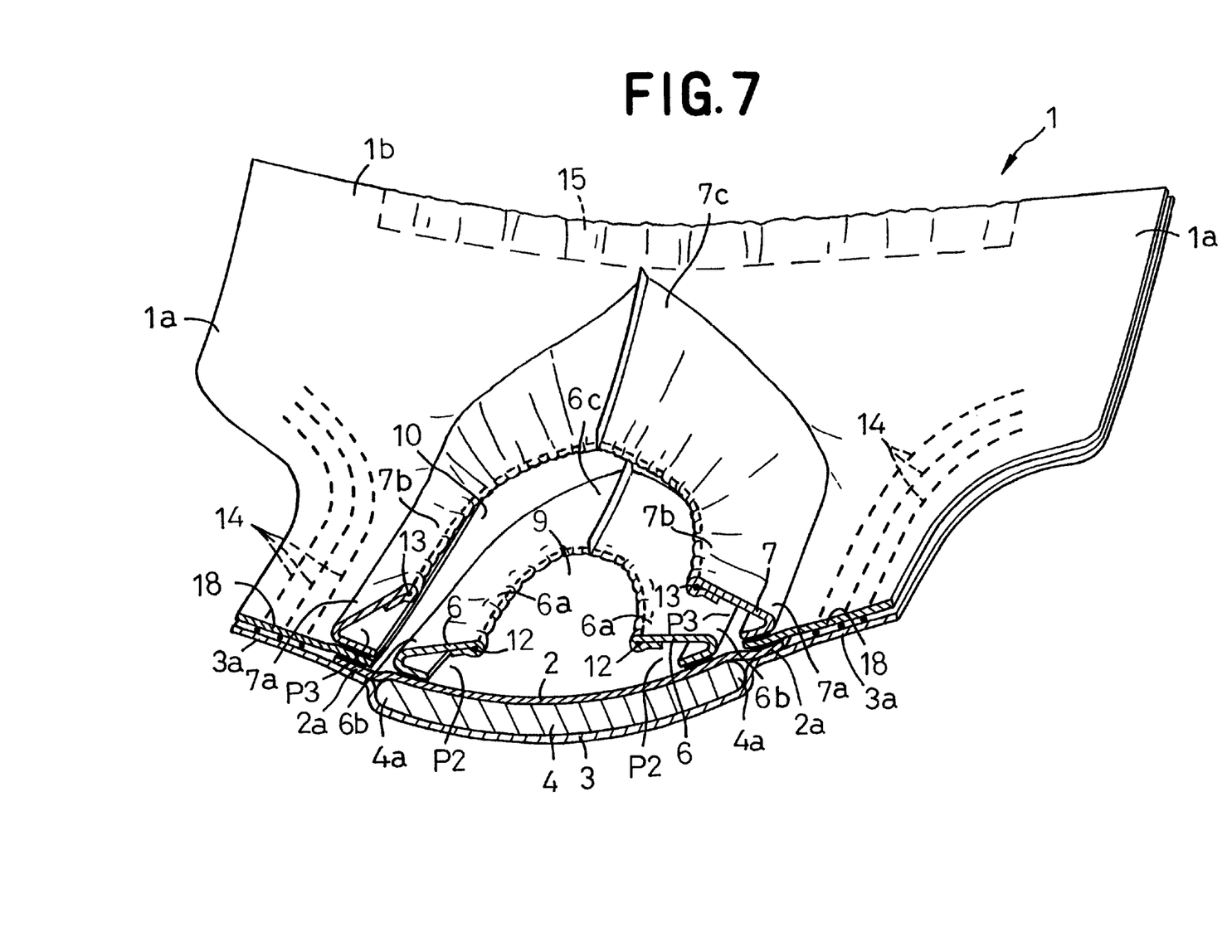
FIG. 7 is perspective view showing the diaper partially in a sectional view taken along line E—E in FIG. 5.
Figure 8:
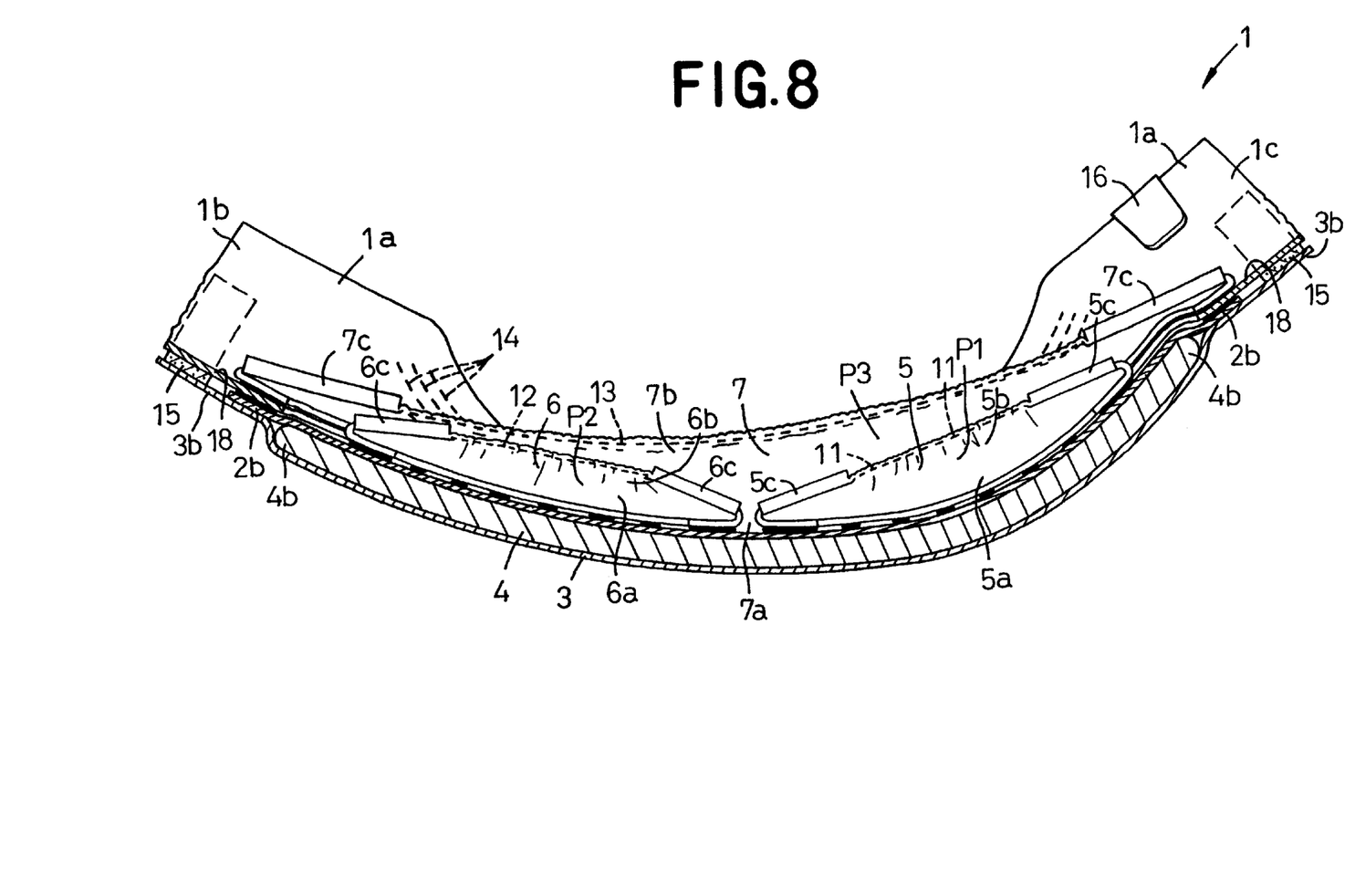
FIG. 8 is a sectional view taken along line F—F in FIG. 5.

FIGS. 6 and 7 are perspective views showing the diaper partially in sectional views taken along line D—D and a line E—E in FIG. 5, respectively, and FIG. 8 is a sectional view taken along line F—F in FIG. 5. The lower peripheral edge portion 7a of the third liquid-barrier wall 7 is partially folded inwardly of the body 1 and fixed to the upper surface of the second topsheet 18 and the upper peripheral edge portion 7b of this third liquid-barrier wall 7 is partially folded inwardly of the body 1 so as to cover the elastic member 13. The longitudinally opposite ends 7c, 7c are put against and bonded to each other along a line extending outward longitudinally of the body 1.

In the body 1, the lower peripheral edge 7a of the third liquid-barrier wall 7 is spaced from the lower peripheral edges 5a, 6a of the first and second liquid-barrier walls 5, 6 so that the topsheet 2 may be exposed between the lower peripheral edge 7a of the third liquid-barrier wall 7, on one hand, and the lower peripheral edges 5a, 6a of the first and second liquid-barrier walls 5, 6, on the other hand. The third liquid-barrier wall 7 cooperates with the topsheet 2 to form a pocket P3 adapted to be opened inwardly of the body 1 as the body 1 is curved longitudinally and transversely thereof with its inner surface inside.

The second topsheet 18 extend outward transversely as well as longitudinally beyond the side edge portions 2a, 2a of the topsheet 2. The second topsheet 18 extend longitudinally outward beyond the longitudinally opposite ends 2b, 2b of the topsheet 2. The transversely opposite side edges 2a, 2a as well as the longitudinally opposite ends 2b, 2b of the topsheet 2 are disposed between the backsheet 3 and the second topsheet 18 and joined to the inner surface of at least one of the backsheet 3 and the second topsheet 18. The backsheet 3 and the second topsheet 18 are joined together in zones along which these backsheet 3 and second topsheet 18 overlap one another. The elastic members 14, 14 for the respective leg-openings as well as the elastic members 15, 15 are disposed between the backsheet 3 and the second topsheet 18 and secured under tension to the inner surface of at least one of these two sheets 3, 18.

Should any amount of urine and feces leak beyond the first and second liquid-barrier wall 5, 6, the third liquid-barrier wall 7 prevents leakage of excretion from occurring along the side edge portions 1a, 1a as well as the front and rear ends 1b, 1c of the body 1. Even when any amount of urine discharged into the second opening 9 leaks beyond the second liquid-barrier wall 6 and flows toward the rear end 1c of the body 1, such amount of urine is reliably absorbed by the body 1 in a zone defined between the respective lower peripheral edges 6a, 7a of the second and third liquid-barrier walls 6, 7 in the front half section 1d of the body 1 and in a zone defined between the respective lower peripheral edges 5a, 7a of the first and third liquid-barrier wall 5, 7 in the rear half section 1e of the body 1. This is for the reason that the amount of urine can flow between the lower peripheral edges 5a, 6a of the first and second liquid-barrier walls 5, 6, on one hand, and the lower peripheral edge 7a of the third liquid-barrier wall 7.

The side edges 3a, 3a of the backsheet 3 and the second topsheet 18 extend transversely outward beyond the side edges 2a, 2a of the topsheet 2 and the longitudinally opposite ends 3b, 3b of the backsheet 3 and the second topsheet 18 extend longitudinally outward beyond the longitudinally opposite ends 2b, 2b of the topsheet 2. This arrangement is effective to prevent urine and feces from permeating the side edges 3a, 3a and the ends 3b, 3b of the backsheet 3 as well as second topsheet 18 even if urine and feces permeate the side edges 2a, 2a and the ends 2b, 2b of the topsheet 2.

The topsheet 2 may be formed by a liquid-pervious sheet such as a nonwoven fabric or a porous plastic film, preferably by a liquid-pervious and hydrophilic sheet. The backsheet 3, the side sheets 17, 17 and the second topsheet 18 may be formed by a hydrophobic nonwoven fabric, a liquid-impervious plastic film or a laminated sheet consisting of such plastic film and hydrophobic nonwoven fabric, preferably by a breathable but liquid-impervious sheet. The first, second and third liquid-barrier walls 5, 6, 7 may be formed by a breathable nonwoven fabric, preferably by a breathable but liquid-impervious nonwoven fabric.

The first—third liquid-barrier walls 5, 6, 7 preferably present their water pressure resistance values defined by a relationship of the first liquid-barrier wall 5>the second liquid-barrier wall 6≧the third liquid-barrier wall 7. More specifically, the first liquid-barrier wall 5 has a water pressure resistance of 150–500 mm, the second liquid-barrier wall 6 has a water pressure resistance of 50–300 mm and the third liquid-barrier wall 7 has a water pressure resistance of 40–200 mm. Generally, feces contains a plenty of organic substances such as protein and lipid and therefore presents a surface tension with respect to these liquid-barrier walls 5, 6, 7 is lower than that presented by urine. In addition to this aspect, it should be taken account that the organic substances contained in feces have an affinity for polyolefine resin. If the nonwoven fabric used as the stock material for the liquid-barrier wall is made of polyolefine resin, feces can permeate this nonwoven fabric more easier than urine. In view of this, the water pressure resistance value of the first liquid-barrier wall 5 is adjusted to be higher than those of the second and third liquid-barrier walls 6, 7 to alleviate a possibility that feces might permeate the nonwoven fabric.

In order that each of these liquid-barrier walls 5, 6, 7 can present an adequately high water pressure resistance, a basis weight of component fibers for the liquid-barrier walls 5, 6, 7 may be increased and, at the same time, interstices of these component fibers may be reduced. It may be contemplated also to form each of these liquid-barrier walls 5, 6, 7 by two or more layers of nonwoven fabric.

The nonwoven fabric may be selected from a group including a spun lace nonwoven fabric, a needle punch nonwoven fabric, a melt blown nonwoven fabric, a thermal bond nonwoven fabric, a spun bond nonwoven fabric and a chemical bond nonwoven fabric. The component fiber for the nonwoven fabric may be selected from a group including polyolefine, polyester and polyamide fibers and polyethylene/polypropyrene or polyester conjugated fiber.

The core 4 comprises a mixture of fluff pulp and highly absorptive polymer particles compressed to a desired thickness and entirely covered with a water-pervious sheet such as tissue paper (not shown). The elastic members 11, 12, 13, 14, 15 may be formed by elastomer such as synthetic or natural rubber or such elastomer previously secured under with tension to a nonwoven fabric. Steps of fixing the core 4, attaching the elastic members 11, 12, 13, 14, 15 and joining of the sheets 2, 3, 5, 6, 7 may be carried out using adhesive such as hot melt adhesive or pressure-sensitive adhesive, or a heat-sealing technique.

This invention is applicable not only to the open-type diaper as shown but also to pull-on or pants-type diaper.

What is claimed is:

1. A disposable diaper having an absorbent body comprising:
   a liquid-pervious topsheet;
   a liquid-impervious backsheet;
   a liquid-absorbent core disposed between said topsheet and said backsheet;
   an annular first liquid-barrier wall having upper and lower peripheral edge portions and extending above an upper surface of said topsheet, the lower peripheral edge portion of said first liquid-barrier wall being folded inwardly of said body and joined to said body so as to define a first opening substantially in a central zone of said first liquid-barrier wall and the upper peripheral edge of said first liquid-barrier wall is elastically stretchable along said first opening, said first liquid-barrier wall lying in a rear half section of said body extending from a vicinity of a center line bisecting a longitudinal dimension of said body toward a rear end portion of said body; and
   an annular second liquid-barrier wall having upper and lower peripheral edge portions and lying in line longitudinally with said first liquid-barrier wall lying in a front half section of said body extending from a center line toward a front end portion of said body, and the lower peripheral edge portion of said second liquid-barrier wall being folded inwardly of said body and joined to said body so as to define a second opening in a substantially central zone of said second liquid-barrier wall and an upper peripheral edge portion having an elastic stretchability along said second opening.

2. A disposable diaper having an absorbent body comprising:
   a liquid-pervious topsheet;
   a liquid-impervious backsheet;
   a liquid-absorbent core disposed between said topsheet and said backsheet;
   an annular first liquid-barrier wall having upper and lower peripheral edge portions and extending above an upper surface of said topsheet, said first liquid-barrier wall being joined along the lower peripheral edge thereof to said body so as to define a first opening substantially in a central zone of said first liquid-barrier wall and the upper peripheral edge of said first liquid-barrier wall is elastically stretchable along said first opening, said first liquid-barrier wall lying in a rear half section of said body extending from a vicinity of a center line bisecting a longitudinal dimension of said body toward a rear end portion of said body;
   an annular second liquid-barrier wall having upper and lower peripheral edge portions and lying in line longitudinally with said first liquid-barrier wall lying in a front half section of said body extending from a center line toward a front end portion of said body, the lower portion of said second liquid-barrier wall being joined to said body so as to define a second opening in a substantially central zone of said second liquid-barrier wall and an upper peripheral edge portion having an elastic stretchability along said second opening; and
   a third liquid-barrier wall having upper and lower peripheral edge portions and spanning said front and rear half sections and extending around said first and second liquid-barrier walls, said lower peripheral edge portion being joined to said body in a vicinity of its periphery so as to define a third opening in a substantially central zone of said third liquid-barrier wall and said upper peripheral edge portion thereof being elastically stretchable along said third opening.

3. A disposable diaper according to claim 2, wherein the respective lower peripheral edge portions of said first and second liquid-barrier walls lie at distances inwardly from the periphery of said body more remote than the upper peripheral edge portion of said third liquid-barrier wall so that entire areas of said first and second openings may be exposed between the lower peripheral edge portions of said first and second liquid-barrier wall and the lower peripheral edge portion of said third liquid-barrier wall.

4. A disposable diaper according to claim 2, wherein the respective upper peripheral edge portions of said first and second liquid-barrier walls lie at distances inwardly from the periphery of said body more remote than the upper peripheral edge portion of said third liquid-barrier wall so that the entire areas of said first and second openings may be exposed in said third opening.

5. A disposable diaper according to claim 2, wherein said first, second and third liquid-barrier walls are formed from a nonwoven fabric and said first, second and third liquid-barrier walls have water pressure resistance values defined by a relationship of said first liquid-barrier wall>said second liquid-barrier wall>said third liquid-barrier wall.

6. A disposable diaper having front and rear regions comprising:
   an absorbent body having a liquid-pervious upper surface and a liquid-impervious lower surface;
   a urine receiving bowl disposed on said upper surface in said front region;
   a feces receiving bowl disposed on said upper surface in said rear region; and
   said urine and feces receiving bowls including annular liquid-barrier walls and openings defined by said walls, respectively, wherein said annular liquid-barrier walls have upper and lower peripheral edge portions and said lower peripheral edge portions are joined to said body while being folded inwardly of said body.

7. A disposable diaper according to claim 6, wherein said diaper further comprises a third receiving bowl disposed on said upper surface so as to surround said urine and feces receiving bowls, and said third receiving bowl includes an annular liquid-barrier wall extending around said liquid-barrier walls of said urine and feces receiving bowls and being spaced apart from outer peripherals of said urine and feces receiving bowls, said third receiving bowl including an opening defined by said wall of said third receiving bowl.

* * * * *